(12) United States Patent
Yamashita et al.

(10) Patent No.: US 6,764,688 B2
(45) Date of Patent: Jul. 20, 2004

(54) METHOD FOR INDUCING IMMUNOSUPPRESSIVE CELLS AND A CULTURE DEVICE TO BE USED THEREFOR

(75) Inventors: Kenji Yamashita, Takasago (JP); Takeshi Fukuchi, Akashi (JP); Tomoko Nishino, Himeji (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/254,170

(22) PCT Filed: Aug. 29, 1997

(86) PCT No.: PCT/JP97/03016
§ 371 (c)(1),
(2), (4) Date: Mar. 2, 1999

(87) PCT Pub. No.: WO98/10055
PCT Pub. Date: Mar. 12, 1998

(65) Prior Publication Data
US 2002/0045252 A1 Apr. 18, 2002

(30) Foreign Application Priority Data
Sep. 3, 1996 (JP) ............................................. 8/233316

(51) Int. Cl.⁷ .......................... A61K 45/00; A61K 47/00
(52) U.S. Cl. .................... 424/278.1; 435/325; 435/366; 435/395
(58) Field of Search ................................ 435/366, 395, 435/325; 424/278.1

(56) References Cited

U.S. PATENT DOCUMENTS 4,925,919 A * 5/1990 Mertelsmann
5,766,920 A * 6/1998 Babbitt et al.
5,958,671 A * 9/1999 Glimcher et al.

FOREIGN PATENT DOCUMENTS

EP          0 421 380          4/1991

OTHER PUBLICATIONS

Chavin et al. J Immunol 152: 3729–3739, 1994.*
Harlow et al. Antibodies A Lab Manual pp. 578–581, 1988.*
Jenkins et al. J Immunol 144: 16–22, 1990.*
Katz et al. Clin. Immunol. & Immunopath. 55:148–155, 1990.*
Moscona et al. In Cells & Tissue Culture Willmer, Ed. pp. 60–61, 1965.*
Schwarz et al. J Immunol 154:5813–5820, 1995.*
JameWay et al Immuno Biology pp. 2:41–243 and 6:2–6:3, 1994.*
Defrancesco, The Scientist 1/5, 1998.*
Bio Whittaker: Adoptive Immunotherapy X–VIVO Product Info, 2002.*
Cao et al. J. Hematother: and Slam Cell Res. 9:183–194, 2000.*
Jixum Lin et al. "CD3 and CD2 Ligation Alters CD49d Epitope expression." *Pathobiology* : 119–132 (1995).
R.A.W. Van Lier et al. "Immobolized anti–CD3 monoclonal antibodies induce accessory cell–independent lymphokine production, proliferation and helper activity in human T lymphocytes." Immunology 68: 45–50 (1989).
Paul Anderson et al. "Crosslinking CD3 with CD2 Using Sepharose–Immobilized Antibodies Enhances T Lymphocyte Proliferation." *Cellular Immunology* 115: 246–256 (1998).
Raymond P. Donnelly and Thomas J. Rogers "Immunosuppression induced by Staphylococcal Enterotoxin B." *Cellular Immunology* 72: 166–177 (1982).
Beverly Z. Packard and Gordon Parry "Bone marrow activation by immobilized antibodies against tumor cells and immunocytes as a potential cancer immunotherapy." *Biochimica et Biophysica Acta.* 1224: 395–400 (1994).
Nguyen et al, *Cellular Immunology, 165(1)*:153–157 (1995).
Wolf et al, *European Journal of Immunology*, 24(6):1410–1417 (1994).
Horwitz et al, *Molecular Immunology*, 30(11):1041–1048 (1993).
Chai et al, *International Immunology*, England, 9(7):935–944 (1997).

* cited by examiner

Primary Examiner—G. R. Ewoldt
(74) Attorney, Agent, or Firm—Sughrue Mion, PLLC

(57) ABSTRACT

The present invention provides a method for inducing immunosuppressive cells by cultivating human cells with the use of a culture device having an affinity for protein and the culture device to be used therefor. According to the present invention, immunosuppressive cells can be efficiently induced by using a solid culture and can provide an efficient therapeutic system for diseases caused by hypersensitivity of the immune system with less side effect.

7 Claims, 7 Drawing Sheets

Rotation in 90 degrees

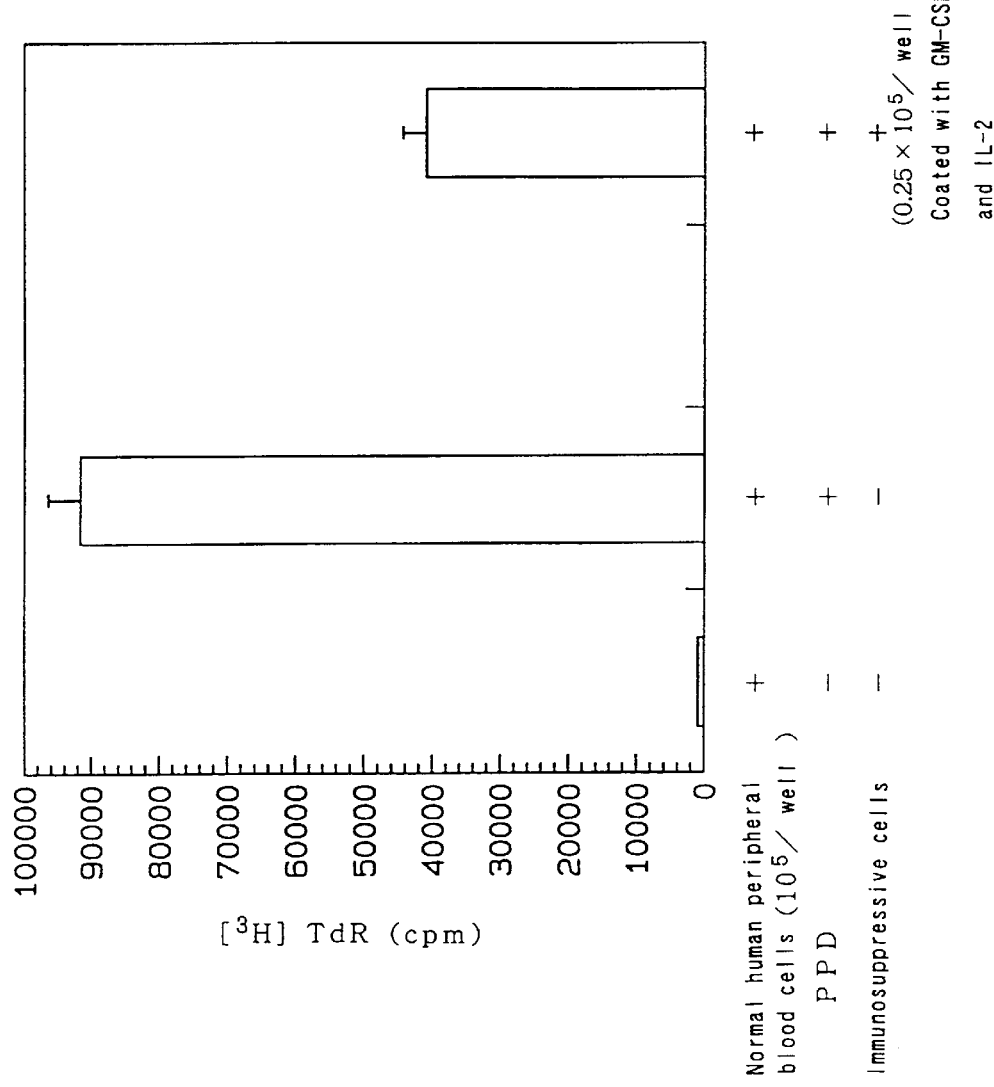

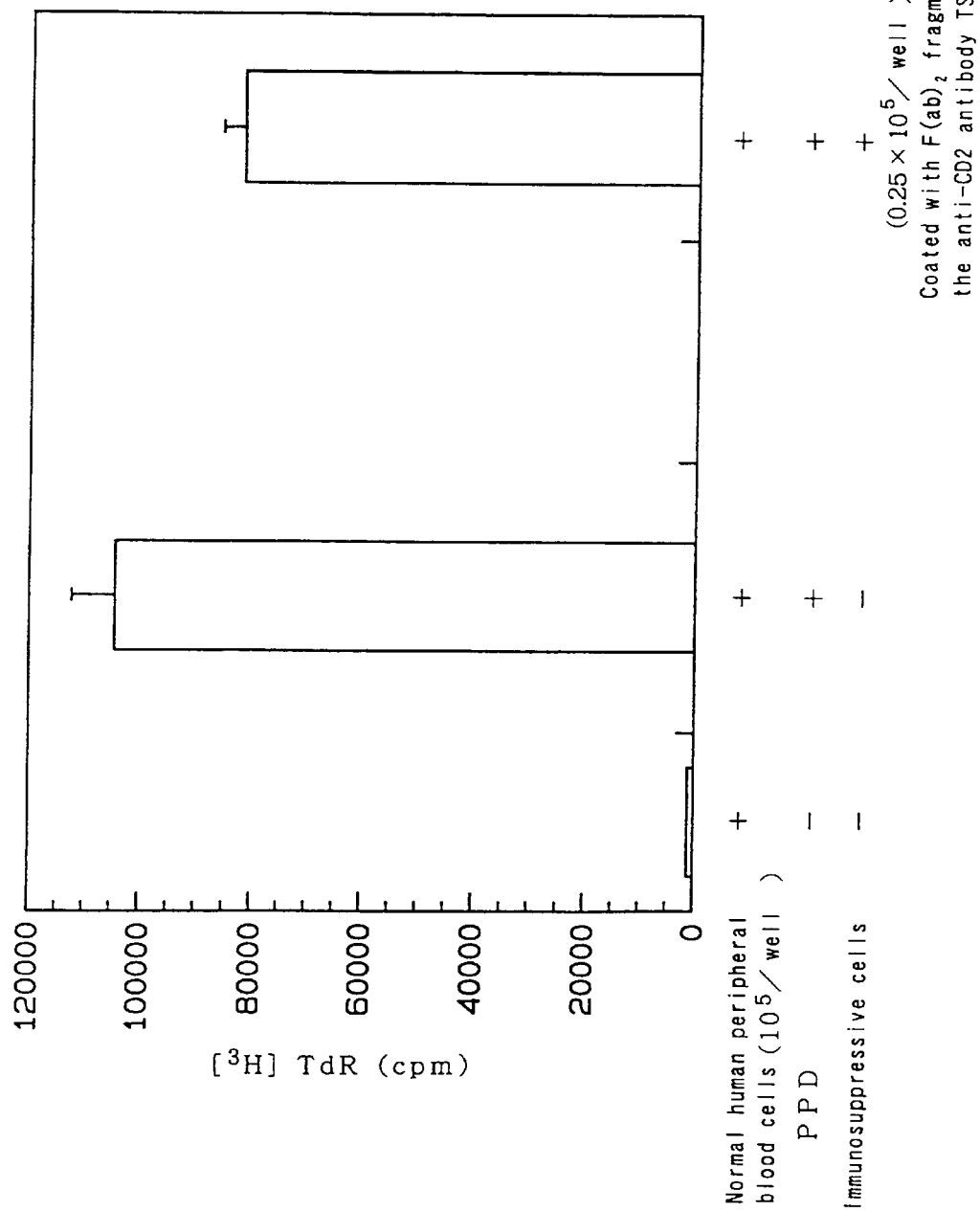

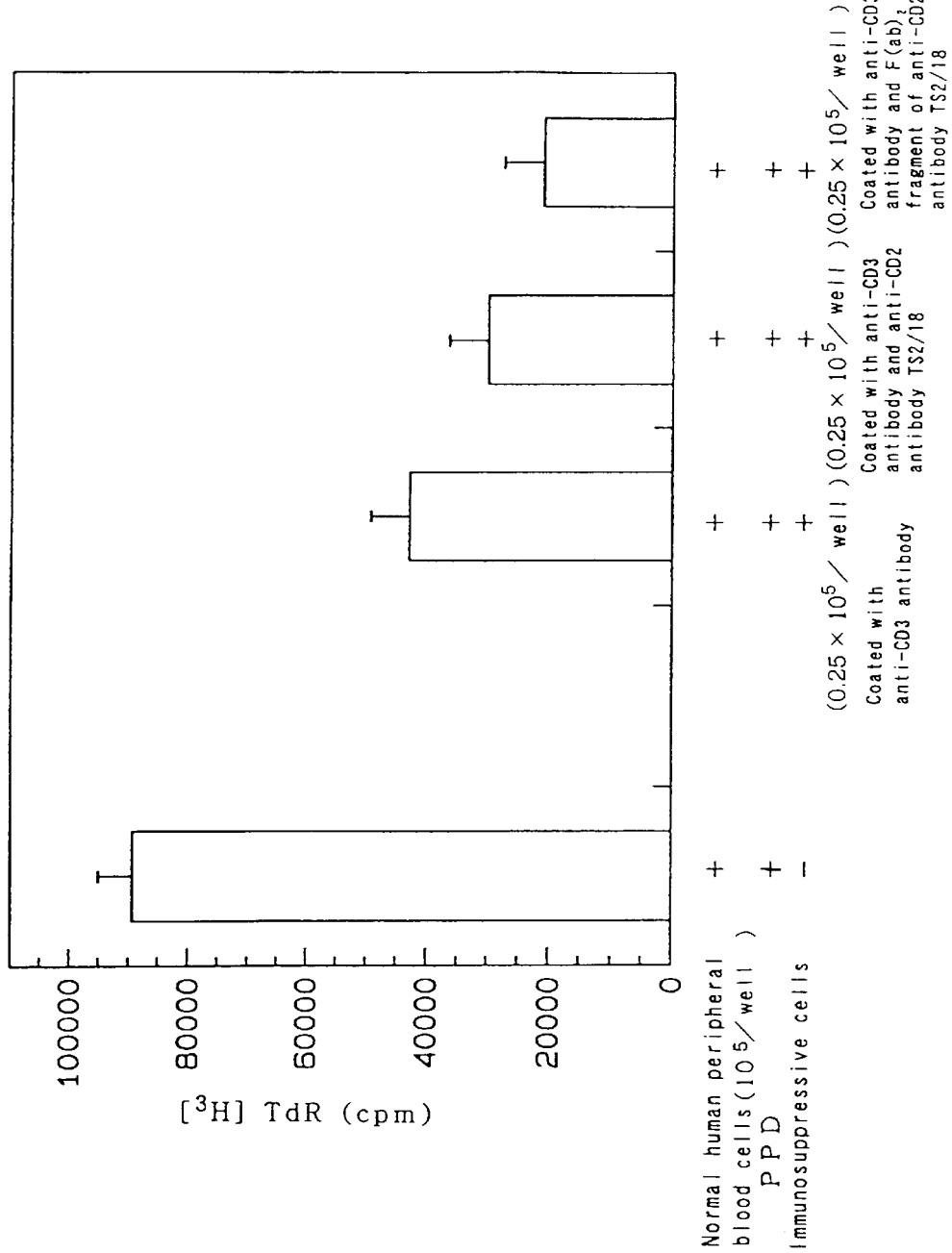

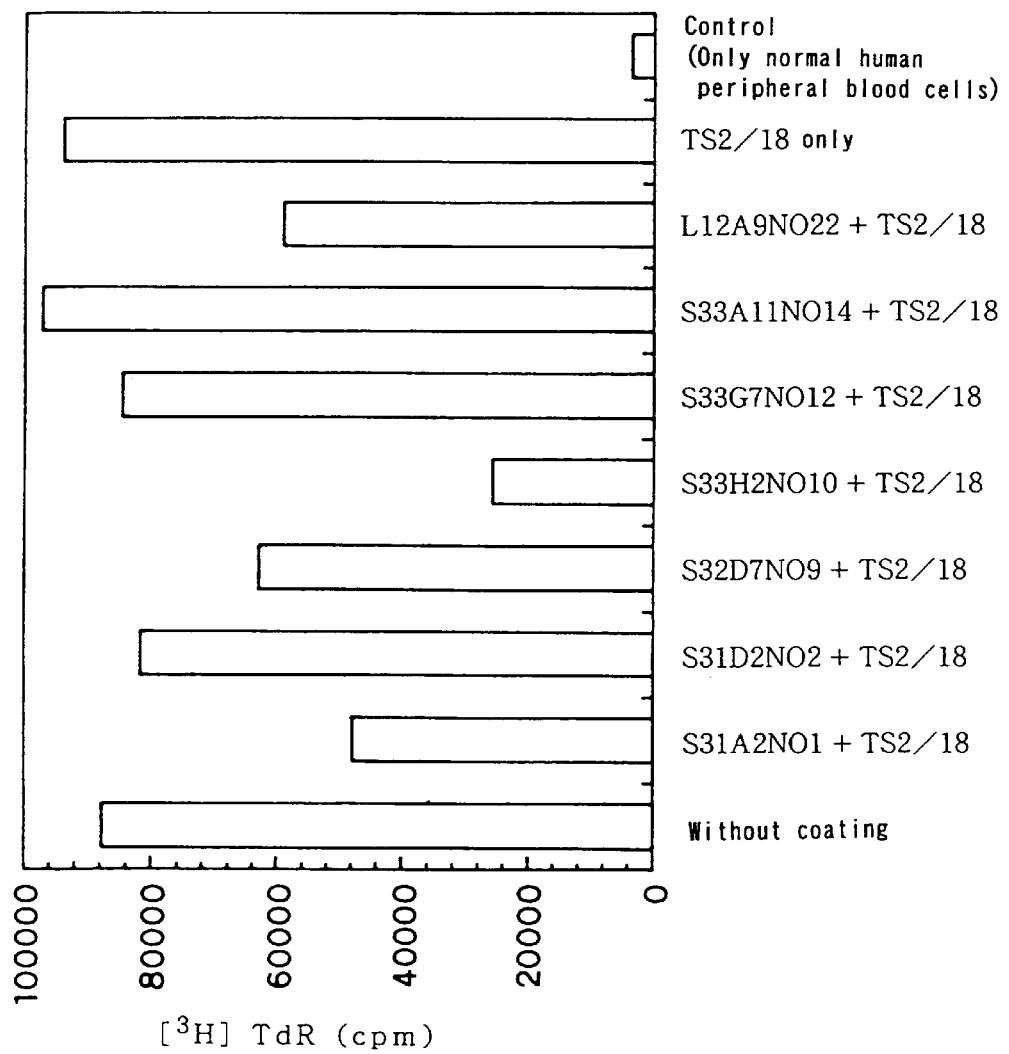

METHOD FOR INDUCING IMMUNOSUPPRESSIVE CELLS AND A CULTURE DEVICE TO BE USED THEREFOR

This application is a 371 national stage application of PCT/JP97/03016, filed Aug. 29, 1997, which claims the benefit of priority to Japan Application No. 233316/96, filed Sep. 03, 1996.

TECHNICAL FIELD

The present invention relates to a method for inducing imniunosuppressive cells and a culture device to be used therefor. More particularly, the present invention relates to a method for inducing immunosuppressive cells by culturing human cells with the use of a culture device having an affinity for protein, and the culture device to be used therefor.

BACKGROUND ART

Autoimmune diseases and rejection in transplantation are caused by the following: host cells recognize self-cells or an organ transplanted as a foreign body and destroy the self-cells or the organ transplanted. Some cases of those diseases show that they are caused by abnormality of immunosuppressive cells in quantity or quality (see Macintosh and Drachman, Science vol. 232, p. 401(1986)). Balashov et al. report that MS (multiple sclerosis) patients show remarkable decrease in efficiency for inducing immunosuppressive T cells due to an autologous mixed lymphocyte reaction and such phenomenon is a cause of an attack of the MS disease (see Balashov et al., Journal of Clinical Investigation, vol. 95, p. 2711(1995)). Accordingly, it is considered that the recovery of the immunosuppressive cells of such patients may be effective in a therapeutic method for such patients. Thus for several examples of inducing immunosuppressive T cells in a system using animals such as mice are reported by, for example, Fresno et al. (see Fresno et al., Journal of Experimental Medicine, Vol. 163, p. 1246 (1980)). Further, as an example of inducing the immunosuppressive cells in human, there is a method utilizing the autologous mixed lymphocyte reaction described in the above reference which has been recently reported. However, this method requires the treatment of a culture medium of human cells with PHA, Con A or anti-CD3 antibody, or adding a plurality of cytokines to the culture. Thus, the method is complicated in operation. Moreover, since the above-mentioned method is suspension culture system, foreign bodies such as lectins (PHA or ConA) used in treatment adhere to the cells. Since those foreign bodies can not be removed completely from the cells by washing, the above-mentioned method still has the possibility of foreign body contamination. Accordingly, the method would never be considered to be desirable and thus, can not be utilized in treatment that targets induction of immunosuppressive cells outside of the body of a patient. The present invention provides an efficient therapeutic system for autoimmune diseases which includes the steps of: taking blood cells out from a patient; effectively inducing immunosuppressive cells, especially immunosuppressive T cells using an immobilized-protein system; and returning the resulting blood cells to the patient.

DISCLOSURE OF THE INVENTION

The present inventors have studied to improve a technique for preparing cells which selectively suppress hypersensitivity of the immune system which causes autoimmune diseases such as those mentioned above, especially immunosuppressive T cells and have completed the present invention.

The present invention provides a method for inducing immunosuppressive cells by culturing human cells with the use of (1) a culture device having an affinity for protein, being previously coated with a protein such as an antibody or a cytokine, or without any coating, or (2) a culture device having an affinity for protein, placing a protein such as the antibody or the cytokine in the device together with the human cells; and the culture device to be used therefor.

That is, the present invention relates to a method for inducing immunosuppressive cells, which comprises culturing human cells with the use of a culture device having an affinity for protein.

Further, the present invention relates to the inducing method, wherein the culture device is previously coated with one or more cytokines or antibodies against surface antigens (claim 2).

Moreover, the present invention relates to the inducing method of, wherein the culture device is previously coated with two or more antibodies against surface antigens, each of said antibodies recognizing different epitope (claim 3).

Further, the present invention relates to the inducing method, wherein human cells and one or more cytokines or antibodies against surface antigens are mixed.

Furthermore, the present invention relates to the inducing method, wherein human cells and two or more antibodies against surface antigens, each of said antibodies recognizing different epitope, are mixed (claim 5).

Moreover, the present invention relates to the inducing method, wherein the antibody against surface antigens is an anti-CD2 antibody or an anti-CD3 antibody.

Further, the present invention relates to the inducing method, wherein the antibody against surface antigens is an anti-CD2 antibody, said anti-CD2 antibody binding to a site of CD2 that participates in the binding of LFA-3 to CD2.

Further, the present invention relates to the inducing method, wherein the antibody against surface antigens is an anti-CD2 antibody, said anti-CD2 antibody binding to a site of CD2 other than a site of CD2 which participates in the binding of LFA-3 to CD2.

Moreover, the present invention relates to the inducing method, wherein two or more antibodies against surface antigens are anti-CD2 antibodies comprising a combination of one or more antibodies which bind to a site of CD2 that participates in the binding to LFA-3 to CD2 and one or more antibodies which bind to a site of CD2 other than the site of CD2 which participates in the binding of LFA-3 to CD2.

Further, the present invention relates to the inducing method, wherein one antibody against surface antigens is the anti-CD2 antibody TS2/18.

Moreover, the present invention relates to the inducing method, wherein one antibody against surface antigens is the $F(ab)_2$ fragment of the anti-CD2 antibody TS2/18.

Further, the present invention relates to the inducing method, wherein the cytokine is IL-2 or GM-CSF.

Moreover, the present invention relates to the inducing method, wherein 0.5 to 10% by volume of serum based on a culture medium is mixed in the culture.

Further, the present invention relates to the inducing method, wherein no serum is mixed with the culture medium in the culture.

Moreover, the present invention relates to the inducing method, wherein a term of the culture ranges between 1 and 7 days.

Further, the present invention relates to the inducing method, wherein the culture device is made of material having an affinity for protein.

Moreover, the present invention relates to the inducing method, wherein culture device is made of plastic material.

Further, the present invention relates to the inducing method, wherein the culture device is made of glass material.

Moreover, the present invention relates to the inducing method, wherein the culture device is a closed plane plate vessel or a closed vessel charged with spherical fine-particles.

Further, the present invention relates to culture device having an affinity for protein, which is used for inducing immunosuppressive cells by culturing human cells.

Moreover, the present invention relates to the culture device, wherein the device is previously coated with one or more cytokines or antibodies against surface antigens.

Further, the present invention relates to the culture device, wherein the device is previously coated with two or more antibodies against surface antigens, each of said antibodies recognizing different epitope.

Moreover, the present invention relates to the culture device, wherein the antibody against surface antigens is anti-CD2 antibody or anti-CD3 antibody.

Further, the present invention relates to the culture device, wherein one or more antibodies that recognize different epitope are the anti-CD2 antibody TS2/18.

BRIEF DESCRIPTION OF THE DRAWINGS

FIG. 4 is a graph that shows the immunosuppressive effect of immunosuppressive cells obtained by the present invention ((b) of EXAMPLE 1) on T cell activation reaction.

FIG. 5 is a graph that shows the immunosuppressive effect of immunosuppressive cells obtained by the present invention ((c) of EXAMPLE 1) on T cell activation reaction.

FIG. 6 is a graph that shows the immunosuppressive effect of immunosuppressive cells obtained by the present invention ((d) to (f) of EXAMPLE 1) on T cell activation reaction.

FIG. 7 is a graph that shows the immunosuppressive effect of immunosuppressive cells obtained by the present invention (EXAMPLE 2) on T cell activation reaction.

BEST MODE FOR CARRYING OUT THE INVENTION

The expression "having an affinity for protein" means having the property that a protein can be immobilized by a bond such as hydrophobic bond, covalent bond or ionic bond.

The culture device of the present invention may be material having an affinity for protein, being non-cytotoxic and being sterilizable. Preferably the device is made of material having an affinity for protein and the material is preferably plastic material or glass material. Plastic material means thermosetting resin or thermoplastic resin. Polymer is more preferable because of its good moldability. Polystyrene is particularly preferable because polystyrene has high affinity for protein and is colorless and transparent. Glass material means silicate, borate, phosphate and the like which solidify without forming crystals (vitrification). Silicate glass is more preferable because of a strong vitrification tendency. Crystallized glass which is formed by heat treatment of silicate glass is particularly preferable because it has a good moldability and good impact resistance. In order to confer an affinity for protein on the culture device, the material may be treated for increasing adsorbability of protein. The usual culture device is coated with protein such as collagen so that the adsorbability of protein is decreased. This is not preferable for the device of the present invention. In the culture device of the present invention, the shape of the material to which cells directly attach is preferably plane shape or spherical shape, because it is necessary to immobilize protein uniformly and further it is necessary that the cells can uniformly and efficiently adsorb thereto. More preferably the culture device is a closed plane plate vessel or a closed vessel charged with spherical fine-particles. As the plane vessel, a usual culture flask, a culture dish, a vessel with a culture plate-like shape, or multistage plate as shown in FIGS. 1(a) to 1(c) can be used.

Figure 1A:
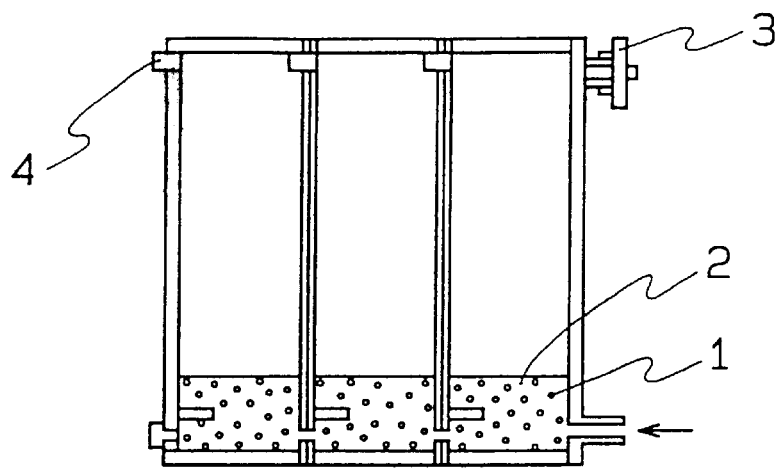
FIG. 1 is an explanatory view of one embodiment of the culture device of the present invention; (a) being a sectional explanatory view of the device when human cells are placed in the device; (b) being a sectional explanatory view of the device (a) being rotated in 90 degrees; and (c) being a top explanatory view of (b).
Figure 1B:
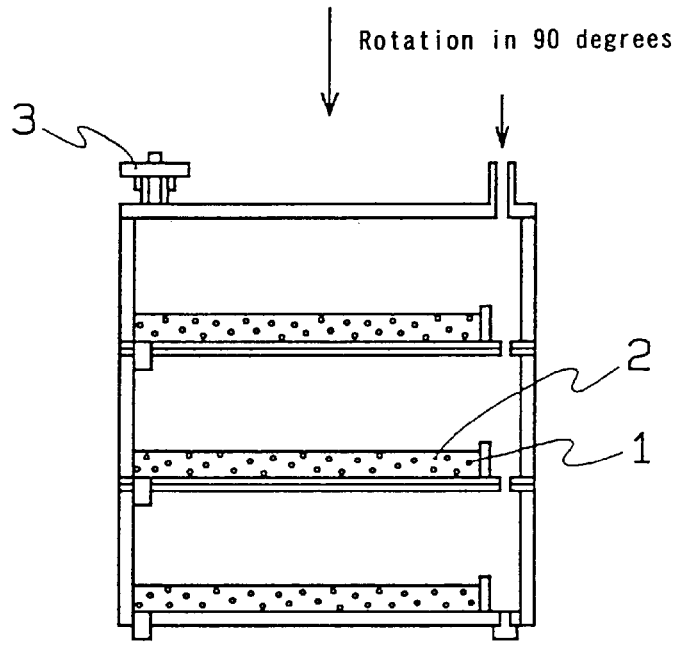
Figure 1C:
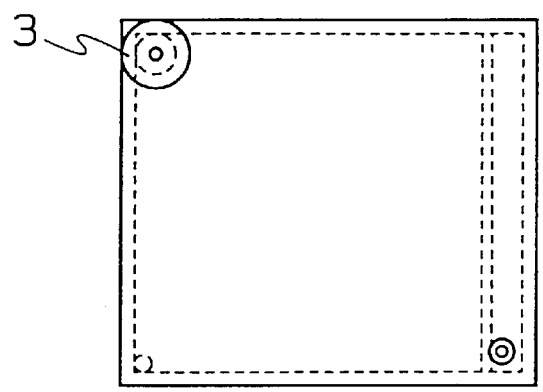

The multistage plate as shown in FIG. 1 is an embodiment of the culture device of the present invention. As shown in FIG. 1(a), a cell suspension (2) containing human cells (1) is placed in the plate from the direction indicated by the arrow. As shown in FIG. 1(b), in the culture the device of FIG. 1(a) is rotated in 90-degrees. During culture, 5% $CO_2$ is passed through the breathable filter (3). The immunosuppressive cells induced can be released by somewhat strongly shaking of the vessel and recovered from the cell recovery opening (4). The FIG. 1(c) is a top view of FIG. 1(b). When such multistage plate is employed, it has the advantages that it can treat many cells at the same time and it can induce plural types of cells having different functions at the same time. For example, by changing the antibody employed for coating, both immunosuppressive cells and cells with ability for activating an immunosuppressive mechanism can be simultaneously induced. When the material of the device is spherical, fine-particles (small spherical beads) can be used in a vessel as shown in FIG. 2.

Figure 2:
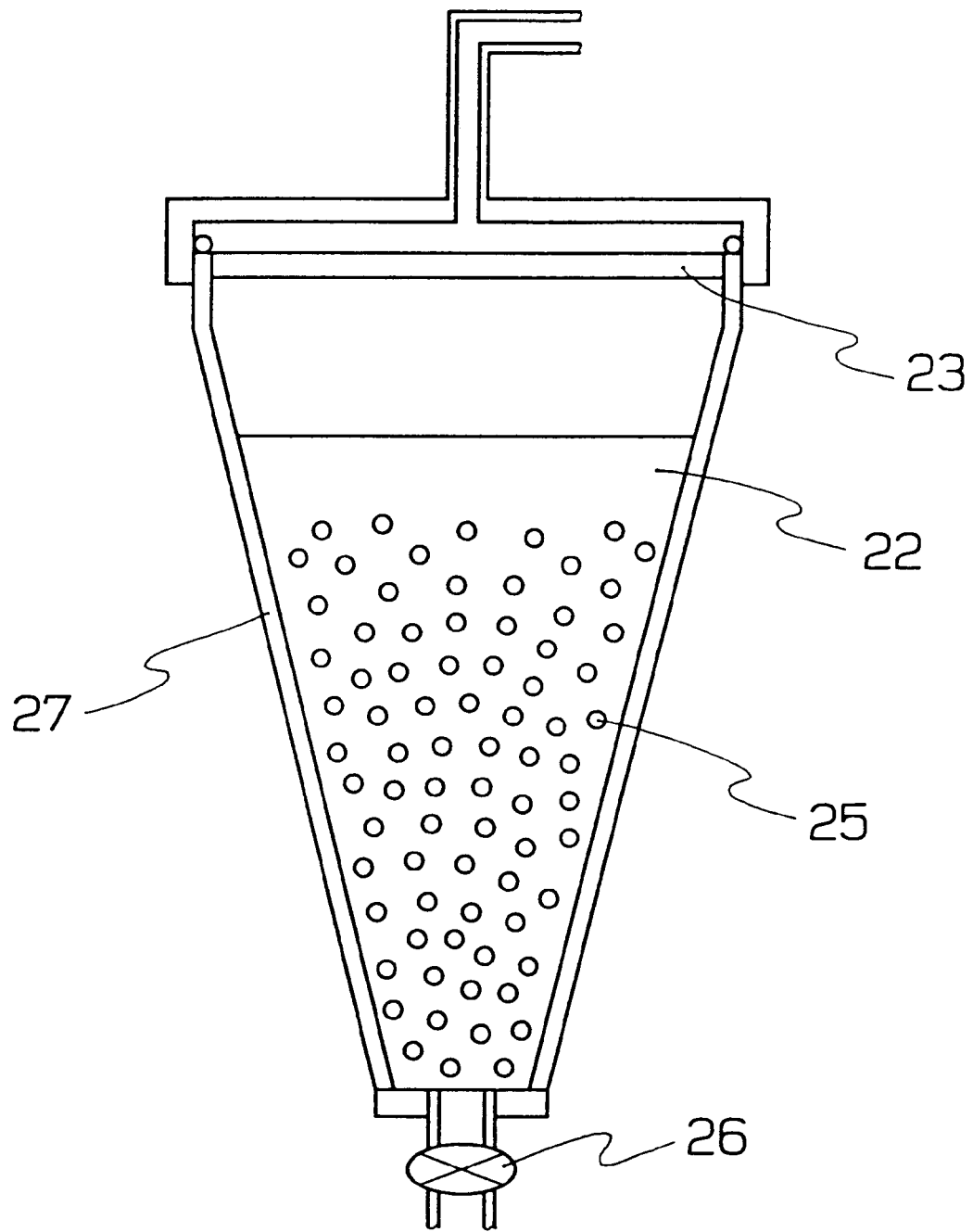
FIG. 2 is a sectional explanatory view of another embodiment of the culture device of the present invention.

The vessel shown in FIG. 2 is another embodiment of the present invention. In FIG. 2, 5% $CO_2$ can be fed to the cell suspension (22) including human cells through the breathable filter (23). The spherical fine-particles (25) are present in the cell suspension (22) and adsorb the human cells. The immunosuppressive cells induced are recovered in the adsorbing form on the spherical fine-particles by opening the stopcock (26). The number (27) shows a side wall. And then, the cells induced can be recovered from the fine-particles by washing the fine-particles with, for example, saline.

In the present invention, a plane plastic plate that is mainly used in ELISA reactions is particularly preferably employed as the device.

The term "human cells" means cells that constitute the human body and cells derived from such cells. As the human cells of the invention, there can be employed, for instance, human peripheral blood cells, human peritoneal cells, human thymocytes, human bone marrow cells, human established T cells and the like. In case that a patient is actually treated by a method wherein cells are entered into the patient, it is most preferable to use the patient's cells in view of immunological rejection or immuno-suppression effect. Among the patient's cells, human peripheral blood cells of the patient are preferable because they are easily collected. Human peripheral blood cells can be prepared from the following: venous blood collected from human is layered on Ficoll (Ficoll-paque, made by Pharmacia Biotech) in a 50 ml polystyrene tube and centrifuged for 20 minutes at 1500 revolutions per minute (rpm), and then, a lymphocyte faction and a monocyte fraction that are formed in a boundary surface are recovered and are washed with RPMI-1640 medium in 3 times (Ficoll centrifugation method). The resulting human peripheral blood cells are inoculated into a culture medium and cultured overnight, and suspension cells are collected to give T cells.

The term "antibody against surface antigens" means an antibody against a protein that mediates intercellular adhesion; an antibody against a protein that, in adhesion, secondarily participates in binding to a molecule on the other cell; and an antibody against a receptor for various cytokines. As the antibody, there can be employed, for instance, an antibody against the immunoglobulin superfamily, an antibody against the integrin superfamily, an antibody against cadherin or an antibody against IL-2 receptor. Among them, the antibody against the immunoglobulin superfamily is preferable, and an antibody having an affinity for CD2 antigen or CD3 antigen of the human T cells or analog thereof is particularly preferable.

The expression "two or more antibodies against surface antigens, each of the antibodies recognizing different epitope" means two or more antibodies that each recognize a different site of a surface antigen molecule as an antigen and bind to each different site. The kind of antibodies is preferably two. As a concrete examples of the antibodies, there can be preferably employed, for instance, two antibodies which recognize CD2 molecule and recognize different epitope. A combination of the anti-CD2 antibody TS2/18 and an antibody which is produced from the hybridoma S33H2NO10 can more preferably be used (see the following REFERENCE EXAMPLE 2, EXAMPLE 2 and TEST EXAMPLE 2). The ratio of the combination of those antibodies is preferably 1:9 to 9:1 (ratio by weight), particularly preferably 1:1 (equivalent weight).

As the "antibody against CD2 antigen (anti-CD2 antibody)", there can be employed, for instance, a monoclonal antibody against each of various epitopes of CD2 or a polyclonal antibody against CD2 molecule or the like. A $F(ab)_2$ fragment of such antibody can also be employed. Among them, the anti-CD2 antibody TS2/18 and the $F(ab)_2$ fragment thereof are more preferable because they have a strong affinity for CD2.

The "anti-CD2 antibody that can bind to a site of CD2 that participates in the binding of LFA-3 to CD2", which is a preferable antibody against surface antigens, means an anti-CD2 antibody with ability for inhibiting the binding of LFA-3 molecule to CD2 molecule. Concretely this type of antibody is judged by measuring as to whether the binding of sheep erythrocyte to a human T cell strain (rosette formation reaction; see Current Protocols in Immunology, vol. 1, section 7.2.1 (1991)) such as human peripheral blood T cells or Jurkat cells (see U. Schnider et al., Int. J. Cancer, vol. 19, p.62 1 (1977)), is inhibited.

The "anti-CD2 antibody that binds to a site of CD2 other than a site of CD2 which participates in binding of LFA-3 to CD2", which is a preferable antibody against surface antigens, means an antibody that does not have the ability for inhibiting rosette formation.

As the "antibody against CD3 antigen (anti-CD3 antibody)", there can be employed, for instance, a monoclonal antibody, a polyclonal antibody or a $F(ab)_2$ fragment thereof that can recognize CD3 molecule. Among them, the anti-CD3 antibody (OKT3) is more preferable because it has a strong affinity for CD3 and T cell-activating ability.

As the "cytokine", there can be employed, for instance, IL-1, IL-2, IL-3, IL-4, IL-5, IL-6, IL-7, IL-8, IL-8 receptor family, IL-9, IL-10, IL-11, IL-12, IL-13, IL-15, GM-CSF, G-CSF, TGF-β, TNF-α, TNF-β, IFN-α, IFN-β, IFN-γ, a macrophage activating factor, a macrophage activating factor, a macrophage migration inhibition factor or the like. Especially, IL-2 and GMCSF are preferable because they are effective in growth of T cells and production of cytokines. Those cytokines can be used alone or in combination thereof. IL-2 and GM-CSF may be isolated from peripheral blood or prepared from a gene recombination method.

The term "immunosuppressive cells" means cells that have the ability to inhibit immune reaction. The measurement of the ability to inhibit immune reaction can be carried out by using a reaction system in which peripheral blood cells prepared from two or more different individuals are mixed (MLR) or a reaction system in which peripheral blood cells from an individual who has T cells (memory T cells) being responsive to a certain antigen, and the antigen are mixed and the like. As explained in the following TEST EXAMPLES 1 and 2, in vitro, cells probably having immunosuppressive activity are mixed with human peripheral blood lymphocytes (hereinafter also referred to as PBL) that is newly obtained from the same person. With the resulting mixture, is mixed PPD (Purified protein derivative; made by Japan B.C.G. Seizo Co., Ltd.) and cultured under the condition at 37° C. with 5% $CO_2$, for several days, followed by mixing of [$^3$H]-thymidine. After culture at 37° C. for an additional 5 to 16 hours, the radioactivity in the cells is counted with a scintillation counter, thereby measuring the ability for inhibiting immune reaction.

Immunosuppressive cells can be obtained by culturing human cells in the culture device or in the culture device to which the antibody against surface antigens and/or the cytokine is immobilized or not immobilized; or immunosuppressive cells can be obtained by culturing human cells in a system where the antibody against surface antigens and/or the cytokine is mixed with the culture medium at the same time, or before or after. In case that human cells are placed in the device at first, a short time for the mixing of the antibody and/or the cytokine (within 3 days) is preferable. More preferably, human cells are placed later (within one day) or at the same time. Particularly preferably, the human cells are placed at the same time. The amount of those protein to be immobilized or placed depends on the protein to be used, and therefore, there is no limitation in particular. The preferable amount ranges between 0.1 and 10 μg/ml against the culture medium. When the amount is too little, induction of immunosuppressive activity may not occur and when the amount is in excess, the cells may be damaged.

As the culture medium, there can be employed, for instance, a culture medium for animal cells, D-MEM or RPMI-1640. Serum may not be mixed or may be mixed with the medium. When serum is mixed, autologous serum is preferably employed. Autologous serum means a serum obtained from the same individual from which the human cells to be cultured are prepared. Autologous serum is the most preferable because cell growth rate is good and non-specific immunoreaction rarely occurs when autologous serum is used. The amount of serum to be mixed is not limited in particular. Generally, the amount ranges between 0.5 and 10% by volume (V/V %). Immunosuppressive cells can be obtained by culturing human cells in the above-mentioned culture medium, usually under the condition at 37° C. with 5% $CO_2$, preferably for 1 to 7 days, more preferably for 1 to 5 days, most preferably for 1 to 3 days.

Since the immunosuppressive cells are induced in the immobilized system, the immunosuppressive cells can be released and recovered by the usual method; for example, by somewhat strongly shaking the culture device.

There is no limitation as to a dosage route for the immunosuppressive cells induced by the method of the present invention; systematic or local administration using medical device such as a catheter is preferable.

The amount of cells to be administered depends on purposes of administration such as the kind of disease and an extent of symptoms of the patient to be administered. They are administered from $10^6$ to $5 \times 10^8$ cells for an adult in a daily dose, preferably from $10^6$ to $10^8$ cells, most preferably from $10^6$ cells.

The present invention provides a simple and efficient method for inducing immunosuppressive cells and also provides a therapeutic method for treating various autoimmune diseases and for suppression of rejection to an organ transplanted.

The present invention will be more specifically described and explained by means of the following EXAMPLES. The present invention is not limited to EXAMPLES.

REFERENCE EXAMPLE 1

Preparation of $F(ab)_2$ fragments of the anti-CD2 antibody TS2/18.

One ml of the antibody solution including 10 mg/ml (PBS) of TS2/18 (American Type Culture Collection (ATCC): HB195) was dialyzed against 200 ml of 20 mM acetate buffer, pH4.5, overnight. After the dialysis, the antibody sample was mixed with 0.25 ml of pepsin-immobilized carrier (made by Pierce) previously equilibrated with 20 mM acetate buffer, followed by incubation with strongly shaking at 37° C. for 4 hours. The reaction was stopped by mixing 1.5 ml of 10 mM Tris-HCl, pH 7.5. The resulting $F(ab)_2$ fragments were isolated using a gel filtration column (Column: Sephacryl S-200, Pharmacia Biotech; Solvent PBS, Flow Rate: 0.6 ml/min).

EXAMPLE 1

Preparation of immunosuppressive cells by culturing human peripheral blood cells using the culture device made of plastic plate Using RPMI-1640 (made by Sigma) including 10%(v/v) (hereinafter referred to as 10%) autologous serum $1.5 \times 10^6$ cells/ml of a normal human peripheral blood cell suspension was prepared from peripheral blood collected from a normal human. Each 100 μl aliquots of the cell suspension were seeded in a total 20 wells in a 96-wells ELISA plate (made by Coming Inc.) and the culture was started (a). Each of 20 wells in 96-wells ELISA plates was previously coated with GM-CSF (made by RD Systems) and IL-2 (made by Becton Dickinson Immunocytometry Systems) in a concentration of 10 μg/ml (PBS) and 20 U/ml (PBS), respectively (b); coated with 10 μg/ml (PBS) of $F(ab)_2$ fragments of the anti-CD2 antibody TS2/18 prepared in REFERENCE EXAMPLE 1 (c); coated with 10 μg/ml (PBS) of the anti-CD3 antibody (OKT3) (made by Orth Diagnostic System Inc.) alone (d); coated with 10 μg/ml (PBS) of the anti-CD3 antibody and 10 μg/ml (PBS) of the anti-CD2 antibody TS2/18 (ATCC:HB195)(e); and coated with a mixture 10 μg/ml (PBS) of the anti-CD3 antibody and 10 μg/ml (PBS) of $F(ab)_2$ fragment of the anti-CD2 antibody TS2/18 at the same time (4° C., overnight)(f). The resulting plates were washed with PBS and therein was placed 100 μl aliquots of $1.0 \times 10^6$ cells/ml (less than the above mentioned cell number) of the normal human peripheral blood cell suspension and the culture was started. After the plates were subjected to culture at 37° C. for 7 days in the 5% $CO_2$ incubator, cells were recovered by pipetting and washed 3 times with PBS, and then the cells were suspended into RPMI-1640 including 10% autologous serum to a final concentration of $3 \times 10^6$ cells/ml.

COMPARATIVE EXAMPLE 1

Coating with cytokines and antibodies on usual culture devices and culture

The culture devices were coated in the same manner as EXAMPLE 1 except that the usual 96-wells culture plates (made by Corning Inc.) were used. The cytokines and antibodies used in coating were washed out.

The human cells were seeded in the same manner as (a) of EXAMPLE 1 into non-coated 20 wells to give cell suspensions.

TEST EXAMPLE 1

Suppression of activation of an antigen (PPD)-specific T cell by immunosuppressive cells obtained from human peripheral blood cells Using RPMI-1640 (made by Sigma) including 10% autologous serum, $1 \times 10^6$ cells/ml of a normal human peripheral blood cell suspension was prepared from peripheral blood collected from the normal human. 100 μl aliquots of the cell suspension were pipetted into a 96-wells round-bottom plate (made by Corning Inc.). PPD (made by Japan B.C.G Seizo Co., Ltd.) was placed in each well to a final concentration of 1 μg/ml. Simultaneously, cells obtained in EXAMPLE 1 (a) to (f) were suspended in RPMI-1640 including 10% autologous serum, and 30 μl aliquots of the cell suspensions including $0.25 \times 10^5$ cells/well and/or $0.5 \times 10^5$ cells/well were placed in each well and cultured for 5 days (in the 5% $CO_2$ incubator, at 37° C.). After mixing 1 μ Ci of [$^3$H] thymidine to each well and culturing for 15 hours, the cells were harvested using a cell harvester (LABO MASH; made by LABO SCIENCE). The radioactivity of $^3$H incorporated in the cells was measured using the scintillation counter LSC-700 (made by Aloka). As a positive control, in wells were placed 30 μl of RPMI-1640 including 10% autologous serum instead of the cells of EXAMPLE 1 and subjected to measurement.

Figure 3:
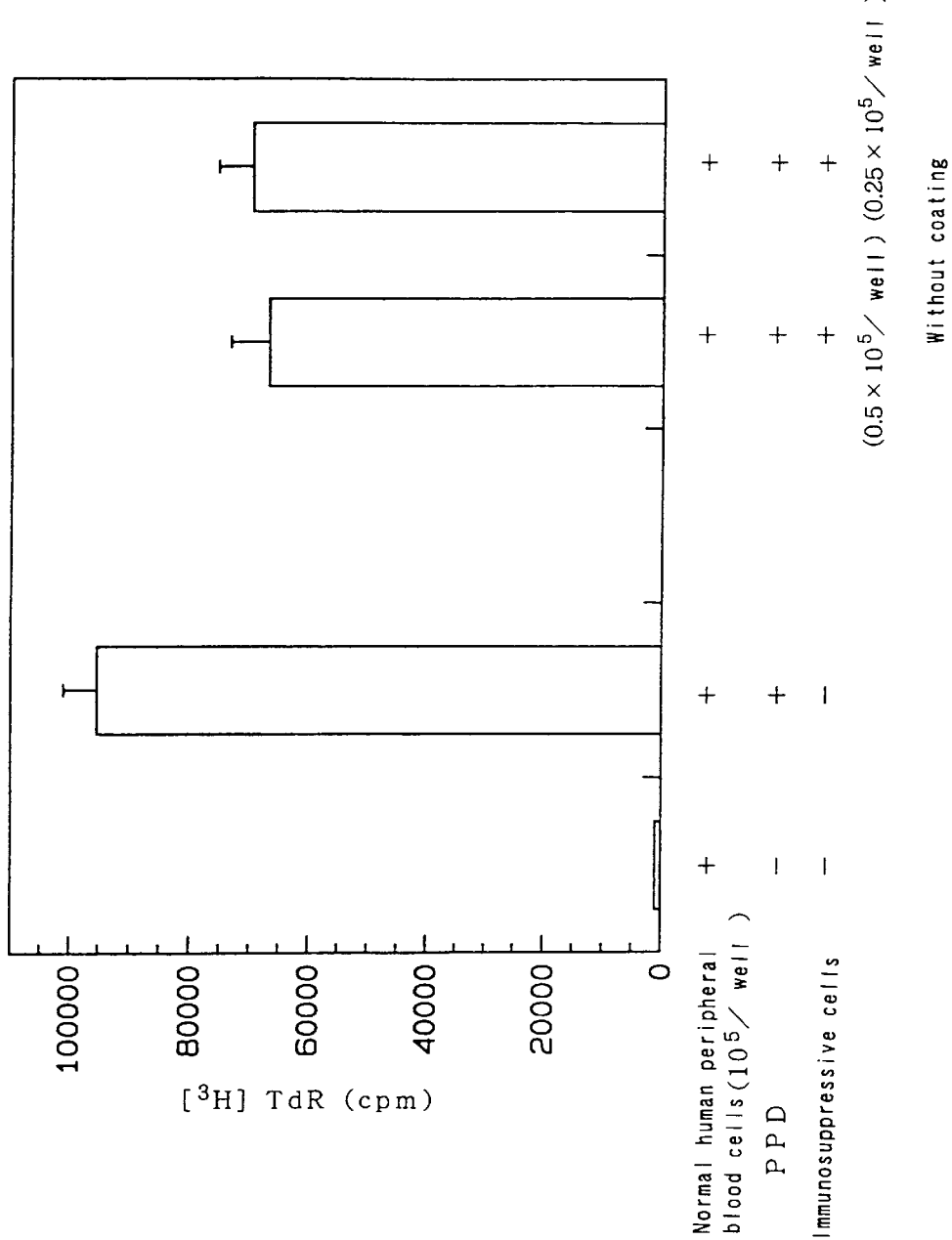
FIG. 3 is a graph that shows the immunosuppressive effect of immunosuppressive cells obtained by the present invention ((a) of EXAMPLE 1) on T cell activation reaction.

The results are shown in FIGS. 3 to 6. When the cells treated in EXAMPLE 1(a) were mixed with one fourth or half of the number of the human cells applied to a PPD-T cell activating system, about 30% suppression was observed (FIG. 3). Where the cells treated in the presence of cytokines in EXAMPLE 1(b) were used, about 55% suppression was observed (FIG. 4). The suppression was about 20% when cells treated in EXAMPLE 1 (c) were used (FIG. 5), and when each of the cells treated in EXAMPLE 1 (d), (e) and (f) was used, about 50%, 67% and 78% suppressions were observed, respectively (FIG. 6).

The cells obtained in COMPARATIVE EXAMPLE 1 were suspended in the culture medium in the same manner as mentioned above and 30 μl aliquots of the cell suspension including $1.0 \times 10^5$ cells/well or $0.5 \times 10^5$ cells/well were placed in each well and cultured as described above.

The result showed about −50% and about −30% suppressions, respectively. That is, when the human cells are cultured in the usual culture device, immunosuppressive cells were not induced, but rather the immunoreaction increased.

REFERENCE EXAMPLE 2

Preparation of anti-human CD2 antibodies Anti-human CD2 antibodies can be prepared by the following: (a) preparing CD2 protein from the human T cell line: Jurkat cell (ATCC TIB (Tumor Immunology Bank) 152); (b) immunizing mice with the resulting CD2 protein to give hybridomas; and (c) screening hybridoma that can produce anti-CD2 antibodies by ELISA using the CD2 protein. The procedures thereof are as follows:

(a) Preparation of the CD2 protein from a Jurkat cells $5.8 \times 10^8$ Jurkat cells were cultured in 2500 ml of RPMI-1640 (made by Sigma) including 10% FCS (Fetal Calf Serum) at 37° C., in the 5% $CO_2$ incubator to a concentration of $7 \times 10^5$ cells/ml and $1.75 \times 10^9$ cells of the clone were subjected to purification. The clones were suspended in 40 ml of lysis buffer (0.01 M Tris-HCl (pH 8.0), 0.15 M NaCl, 1% Triton X-100, 1 mM iodeacetoamide (made by Sigma), 1 mM PMSF), and treated with the mini disk rotor (made by Biocraft) at 4° C. for 1 hour. Then, after centrifugation at 3615×g at room temperature for 15 minutes, NaDOC (Sodium deoxycholate: made by Sigma) was mixed to a final concentration of 0.5% NaDOC and supernatant was recovered by ultracentrifugation (at 158,000×g, 4° C., for 60 minutes). The resulting sample was subjected to purification using the antibody column as a Jurkat-purified supernatant.

The antibody column was prepared using Affi-Gel 10 (made by BioRad Laboratories, Inc.) as a carrier by immobilizing the anti-CD2 antibody TS2/18 (ATCC HB195) on the carrier (1 mg/ml gel). Econo-column($\phi$: 1 cm, Height: 10 cm, made by Bio-Rad Laboratories, Inc.) was charged with 5 ml of immobilized gel. The sample was loaded (1 ml/min), washed with 50 ml of PBS, followed by elution using 100 ml of elution buffer (0.1 M tri-sodium citrate (pH3)). The sample eluted was brought to neutral pH by using the neutralization buffer (1 M Tris-HCl (pH 11)).

The elution buffer was replaced by PBS with the dialysis cassette (made by Pierce), and the protein content in the sample was measured. As a result, it was confirmed that about 150 μg of CD2 protein was obtained. Further, as the antigen for immunization the antigen purification with PEG 20,000 (made by Wako Pure Chemical Industries, Ltd.) was employed.

(b) immunization of mice by CD2 protein and isolation of hybridomas

The purified human CD2 obtained in the above (a) was mixed with a complete adjuvant Titer MAX (made by CytRX Corporation). The resulting mixture was peritoneally injected into 5-week old Balb/c mice (purchased by Japan SLC Co., Ltd.) a total of 4 times at an interval of a week (25 μg g/time/mouse). Antibodies raised in the mice immunized were subjected to titer confirmation by ELISA using the plate coated with CD2 protein (confirmation as to whether sufficient titer of antibodies were obtained), and the spleens were removed from the mice. A fifteen ml spleen cell suspension was prepared with IMDM (made by Sigma)/10% FCS culture medium. Then, the suspension was centrifuged at room temperature at 1000 rpm for 10 minutes and cells were recovered. Ten ml of 0.17 M $NH_4Cl$ was mixed with the cells for hemolysis. Again the suspension was centrifuged in the same manner as described above, and suspended into 10 ml of IMDM/10% FCS culture medium to prepare a solution including $1 \times 10^8$ cells of the spleen cells.

To prepare the hybridomas, the spleen cells and mouse myeloma cells SP2/O-Ag44 (ATCC CRL (Cell Repository Lines)1581) were used. The cells were washed with IMDM culture medium and prepared to a final concentration of $2 \times 10^7$ to $3 \times 10^7$ cells.

The cells were fused by mixing the spleen cells and the myeloma cells at a ratio of 5:1 (spleen cells: $1 \times 10^8$ cells and myeloma cells: $2 \times 10^7$ cells), and the resulting fused cells were centrifuged at room temperature at 1000 rpm for 5 minutes, and then recovered. After the cells were washed with 30 ml of IMDM culture medium, 2 ml of 50% PEG 1500 (made by Boehringer Mannheim GmbH) was slowly mixed therewith, and with strongly shaking for 1 minute, 4 ml of IMDM culture medium was slowly mixed therewith for 2 minutes. Another 16 ml of IMDM culture medium was mixed therewith for 2 to 3 minutes, and again centrifuged in the same manner as mentioned above, and cells were recovered. Next, the resulting cells were suspended in 5% briclone (made by Dainippon Pharmaceutical Co., Ltd.)-HAT (made by GIBCO BRL)-IMDM/10% FCS culture medium to give a suspension of $3 \times 10^6$ cells/ml. The cells were seeded in a 96-wells flat-bottom plate (made by IWAKI GLASS) at 100 μl/well. After 7 days culture at 37° C. in the 5% $CO_2$ incubator, the culture medium was exchanged to HT(made by GIBCO BRL)-IMDM/10% FCS. The culture medium was changed every 3 days to isolate the hybridomas.

(c) Selection of anti-CD2 antibody-producing hybridomas

50 μl of human CD2 solution (5 μg/ml PBS) prepared in the above-mentioned method (a) was placed in each well of a 96-well ELISA plate (made by Corning Inc.) and coating with the solution occurred at 4° C. overnight. After washing with PBS/0.05% Tween 20, a blocking treatment was performed using 4-times diluted Blockace (made by Nakalai Tesque) for 2 hours at room temperature. After washing with PBS/0.05% Tween 20, 50 μl aliquots of supernatant of the hybridomas were placed in each well and left for 1 hour at room temperature. After washing with PBS/0.05% Tween 20, 1000-times diluted anti-mouse IgG antibody labeled with HRP (Horse Radish Peroxidase)(made by Cappel) was mixed therewith, let stand for 1 hour at room temperature, washed with PBS/0.05% Tween 20, and 100 μl of chromophore liquid (10 mg of O-phenylenediamine tablet (made by Sigma), and 10 μl of $H_2O_2$ dissolved in citrate-phosphate buffer), was mixed therewith and reacted for 10 minutes. The colored clones were selected as the anti-CD2 antibody-producing hybridoma.

EXAMPLE 2

Preparation of human peripheral blood cells cultured with antibody-immobilized plastic plate Among the hybridomas obtained in REFERENCE EXAMPLE 2, seven clones with high reactivity in ELISA were selected. The clones were cultured in serum-free medium at 37° C., in the 5% $CO_2$ incubator for 4 days and thus culture media including each antibodies were obtained. Then, each of those antibody-including media and anti-CD2 antibody TS2/18 were coated on each of 20 wells of a 96-well ELISA plate (made by Coming Inc.) (10 μl of the culture medium of each clone and 0.5 μg of TS2/18 were placed in each well and left at 4° C. overnight). After washing with PBS, 100 μl aliquots of normal human peripheral blood cell suspension adjusted to a concentration of $1.0 \times 10^6$ cells/ml using RPMI-1640 (made by Sigma) including 10% autologous serum were seeded to each well. Similarly 100 μl aliquots cell suspension were seeded into 20 wells coated with 0,5 μg of TS2/18 alone and into 20 wells without coating. After incubation at 37° C. in the 5% CO2 incubator for 7 days, the cells in each of the 20 wells were recovered and washed with PBS 3 times. Then, the cells were suspended in RPMI-1640 culture medium (made by Sigma) including 10% autologous serum to a final concentration of $3 \times 10^6$ cells/ml.

TEST EXAMPLE 2

Evaluation of the suppression ability of the cells treated with the immobilized antibody on antigen (PPD)-specific T cell activation reaction Into a 96-well round-bottom plate (made by Corning Inc.) 100 μl aliquots of normal human peripheral blood cell suspension adjusted to $1.0 \times 10^6$ cells/ml using RPMI-1640 (made by Sigma) including 10% autologous serum were poured. PPD (made by Japan B.C.G. Seizo Co., Ltd.) was placed in each well to a final concentration of 1 μg/ml. Simultaneously, 30 μl aliquots of cell suspensions including $10^5$ cells/well of the cells prepared in EXAMPLE 2 were placed in the wells and cultured for 5 days (in the 5% $CO_2$ incubator, at 37° C.). Then, 1 μ Ci of [$^3$H] thymidine was placed in each well, cultured for 15 hours, and the cells were harvested using a cell harvester (LABO MASH, made by LABO SCIENCE). The radioactivity of $^3$H incorporated in the cells was measured using the scintillation counter LSC-700 (made by Aloka).

As shown in FIG. 7, four clones (S31A2NO1, S32D7NO9, S33H2NO10 and L12A9NO22) out of seven clones were found to significantly suppress the PPD-T cell activation reaction when combined with TS2/18. The suppression rates thereof were S31A2NO1 (47%), S32D7NO9 (29%), S33H2NO10 (74%) and L12A9NO22 (34%), respectively. Especially, the system employing the clone S33H2NO10 was observed to induce strongly immunosuppressive cells. The present experiment was performed in n=2, and the value in the Figures are averages of the experiments.

INDUSTRIAL APPLICABILITY

According to the present invention, immunosuppressive cells can be induced efficiently by the immobilized culture. Therefore, the present invention can provide an efficient therapeutic system with fewer side-effects by which diseases with hypersensitivity of the immune system can be efficiently treated.

We claim:

1. A method of inducing immunosuppression comprising (a) inducing immunosuppressive cells, by culturing human peripheral blood cells, in a culture device previously coated with an anti-CD3 antibody and an F(ab)$_2$ fragment of the anti-CD2 antibody TS2/18 produced from hybridoma HB-195 (ATCC Accession number HB-195), and (b) placing said immunosuppressive cells in a human.

2. The method of inducing immunosuppression of claim 1, wherein 0.5–10% by volume of serum based on a culture medium is mixed into the culture medium.

3. The method of inducing immunosuppression of claim 1, wherein no serum is present in the culture medium.

4. The method of inducing immunosuppression of claim 1, wherein the culture duration ranges between 1 and 7 days.

5. The method of inducing immunosuppression of claim 1, wherein the culture device is made of plastic material.

6. The method of inducing immunosuppression of claim 1, wherein the culture device is made of glass.

7. The method of inducing immunosuppression of claim 1, wherein the culture device is a closed plane plate vessel or a closed vessel charged with spherical fine-particles.

* * * * *